United States Patent [19]

Heilman et al.

[11] 4,003,369
[45] Jan. 18, 1977

[54] ANGIOGRAPHIC GUIDEWIRE WITH SAFETY CORE WIRE

[75] Inventors: Marlin S. Heilman, Gibsonia; Seid W. Waddell, Tarentum, both of Pa.

[73] Assignee: Medrad, Inc., Pittsburgh, Pa.

[22] Filed: Apr. 22, 1975

[21] Appl. No.: 570,999

[52] U.S. Cl. .............................. 128/2 M; 128/205
[51] Int. Cl.² .......................................... A61B 5/02
[58] Field of Search ........ 128/2 M, 2.05 R, DIG. 9, 128/DIG. 14, DIG. 16, 348

[56] References Cited
UNITED STATES PATENTS

| | | | |
|---|---|---|---|
| 3,452,742 | 7/1969 | Muller | 128/2 M |
| 3,731,671 | 5/1973 | Mageoh | 128/2.05 R |
| 3,789,841 | 2/1974 | Antoshkiw | 128/2.05 R |
| 3,906,938 | 9/1975 | Fleischhacker | 128/2 M |

*Primary Examiner*—Louis G. Mancene
*Assistant Examiner*—Robert F. Cutting
*Attorney, Agent, or Firm*—Fleit & Jacobson

[57] ABSTRACT

There is disclosed a catheter guidewire and a method for manufacturing the guidewire. In one embodiment, the guidewire is developed from a coiled semi-rectangular flatwire which has been coated with a surface lubricant such as Teflon prior to winding. In another embodiment, the flatwire is wound, polished by abrasion and then electropolished. A combination safety core wire extends longitudinally within the coiled guidewire and is welded to the respective ends of the guidewire. The safety core wire is a cylindrical wire whose uniform main body is smoothly tapered into an ultra-flexible flattened distal tip by means of combined mechanical metal forming and electro-etching techniques.

10 Claims, 16 Drawing Figures

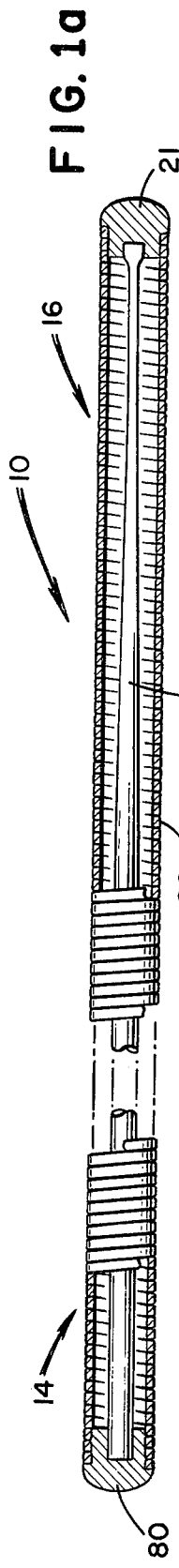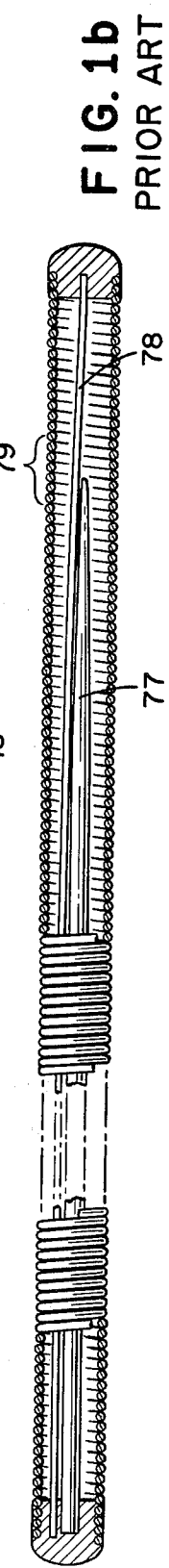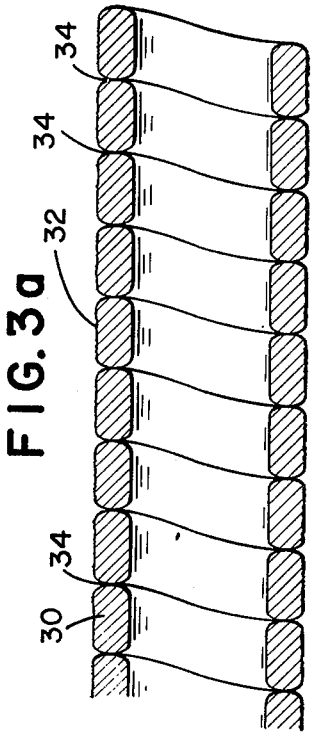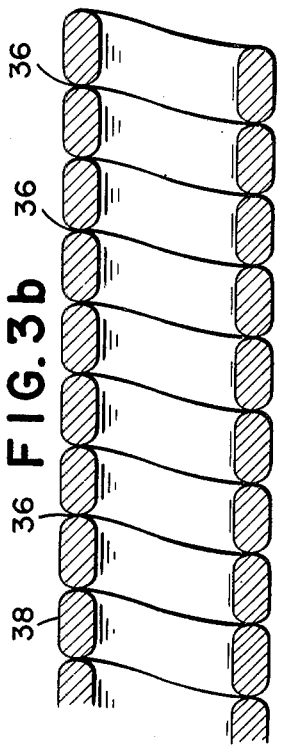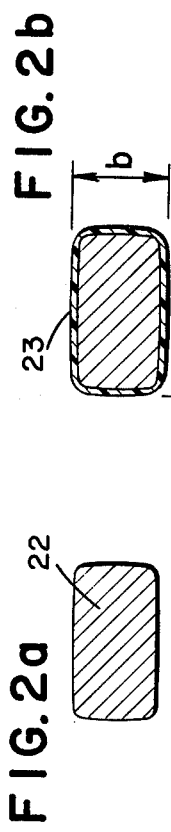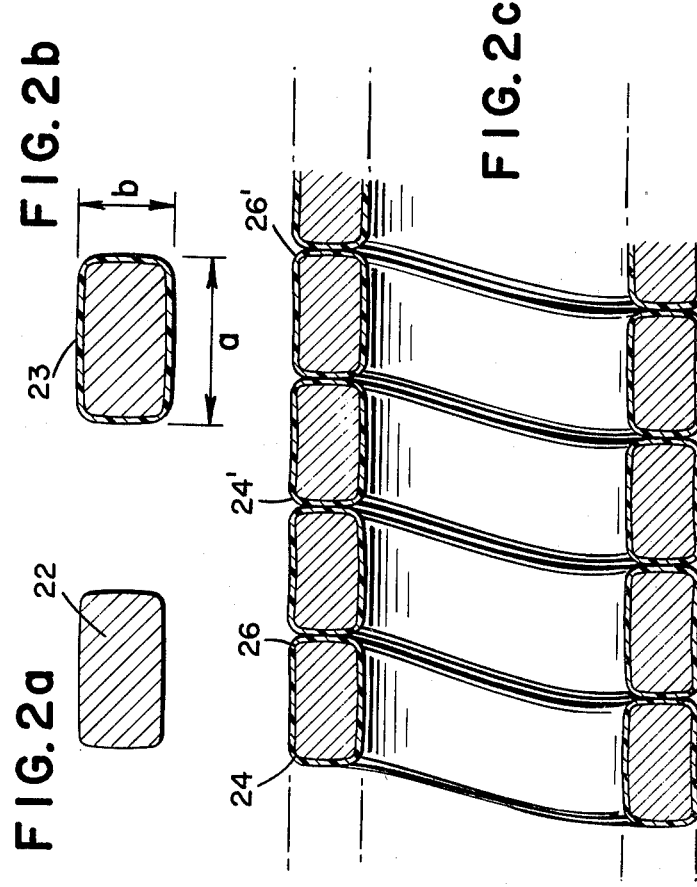

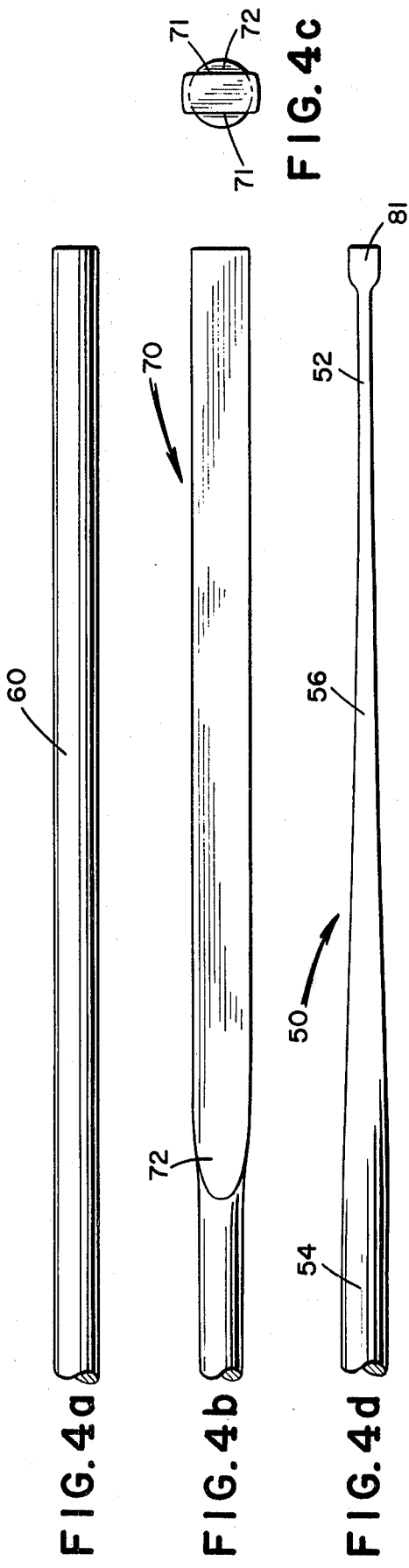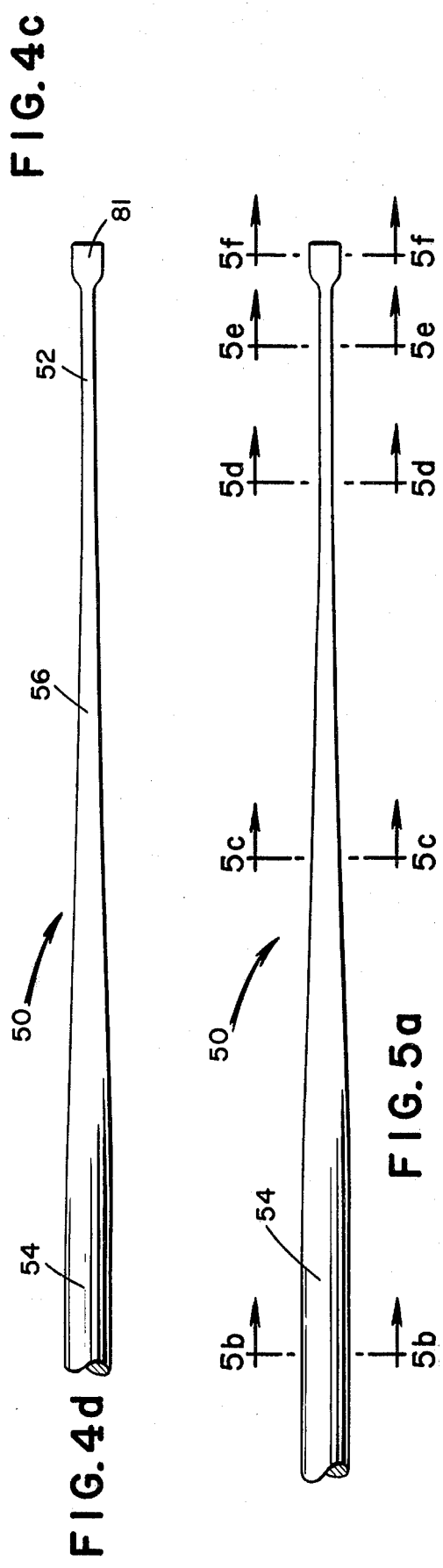

ANGIOGRAPHIC GUIDEWIRE WITH SAFETY CORE WIRE

BACKGROUND OF THE INVENTION

The present invention relates to catheters, and more particularly, to catheter guidewires and core and safety wires for use therewith.

Current techniques of introducing a catheter into the vascular system of a patient include the followng steps: insertion of a sharp cannula through the skin and into the vascular system, insertion of a spring guidewire through the cannula and into the vascular system, and removal of the cannula from the patient's body and insertion of the catheter into the body by sliding said catheter over the guidewire. The guidewire is then withdrawn, and the catheter is ready for further positioning and use.

It should be evident that the guidewire must be flexible and yet strong. It must be flexible enough to negotiate the desired tortuous path of the vascular system and do no damage with its leading tip portion and yet be strong enough to resist doubling back, kinking or breaking during the insertion and retraction procedures. It is accordingly desirable that the guidewire have a flexible and yet guidable distal tip, and a relatively stiff, strong elongated body portion. In addition to the foregoing, the guidewire should have an ultra-smooth outer surface.

A guidewire, sometimes referred to as a spring guide, is constructed of a finely wound spring with one or more wires running longitudinally within the spring's central lumen. More detailed structure and function will be explained later.

An ultra-smooth outer guidewire surface is desirable because rough surfaces can traumatize the patient's tissues during movement of the guidewire. In addition, a smooth guidewire surface facilitates cleaning, thus minimizing the possibility of introducing potential toxic or pyrogenic material to the patient's system.

While to the naked eye, the outer surface of a typical guidewire will appear smooth, microscopic surface irregularities are oftentimes present.

Any biologically foreign material introduced into the bloodstream may initiate blood clots (thrombosis). Such thrombogenicity is an undesirable side effect of known angiographic guidewires, increasing the possibility of generating blood clot emboli in the vascular system with the angiographic procedure. Blood clot generation (thrombosis) may be partially a function of the quantity of foreign material surface area. It is well known that surface roughness may multiply the actual exposed surface area of a material many times over a equivalent quantity of smooth area. Thus surface smoothness in itself is a factor in thromboresistance.

An existing approach to a blood clot resistant guidewire surface has been the chemical bonding of an anticoagulant material to the guidewire surface. The present invention offers a novel alternative to a chemically bonded anticoagulant.

One known type of guidewire is developed from a coiled flatwire which forms the outer casing. As used here, a flatwire has an approximately rectangular cross section. While the flatwire has several properties which are favorable to its use as a guidewire outer casing such as increased strength and resistance to fracture, it also has drawbacks. Due to internal forces which are developed during the required winding, or coiling operation, the flatwire tends to take a concave shape across its periphery, becoming somewhat sharp at its edges. Some attempts have been made to overcome this drawback of concavity with edging by coating or grinding the wires after winding. However, neither coating nor grinding has been found satisfactory because coatings often crack during guidewire flexing and grinding still leaves microscopic surface irregularities.

Structural integrity with flexibility is another requisite for a successful guidewire. A broken guidewire, with the possibility of leaving debris in the patient's body cannot be tolerated. A commonly employed precaution against leaving a broken guidewire tip in the vascular system of a patient, is the provision of a thin wire termed a safety wire inside the wound outer guidewire casing. The safety wire is customarily soldered both to the proximal and distal ends of the guidewire to enable the removal of a broken distal fragment should a break occur in the outer spring or guidewire casing. Then, to provide some degree of rigidity to the guidewire body, a core wire is frequently positioned coextensive with the safety wire, inside the outer casing of the guidewire, and connected to the proximal end but ending freely several centimeters short of the guidewire distal tip. Such a structure as this has resulted in the problem that there is a semi-abrupt change from rigidity to flexibility at the body tip junction. Such a change of flexibility may produce a breakpoint when the guidewire is subjected to repeated flexion.

One might postulate that by tapering the core wire down to a thin flexible tip portion that the breakpoint could be eliminated. However, if this portion is free and not connected distally, such a thin free tip portion could protrude from the spring casing with excessive flexion and rough handling of the guidewire. An interesting alternative would be to taper down the core wire to achieve the desired flexibility and connect the tip to the end of the guidewire thus combining the functions of the safety wire and core wire into one safety-core wire. In practice one manufacturer has done essentially this by grinding a taper on the core wire and soldering a braid to the core wire tip which in turn is connected to the tip of the guidewire. Another approach has been to grind a taper followed by a reduced diameter tip portion which is subsequently rolled to a flattened cross-sectional configuration. The first alternative is labor intensive and adds an extra solder connection. The second method runs a risk of weakening or damaging the safety-core wire from the secondary operations of grinding and rolling.

The guidewire of the present invention overcomes the above drawbacks.

SUMMARY OF THE INVENTION

Briefly, the present invention relates to a guidewire having a wound outer casing with an ultra-smooth surface, and an integral safety-core wire for ensuring structural integrity of the guidewire without impairing guidewire flexibility at the distal tip. A method of manufacturing the guidewire forms another aspect of the present invention.

In one embodiment of the present invention, the ultra-smooth outer surface of the wound guidewire is developed by coating the base flatwire with a lubricating agent such as Teflon, prior to being spring-wound. In this manner, flaking of the outer coating is minimized during bending of the guidewire when in use. In another embodiment, the surface is smoothed by first lightly grinding the surface of the spring-wound flatwire by abrasion, and subsequently electropolishing the guidewire surface.

The inventive safety-core wire extends longitudinally through the guidewire outer casing and is attached to the casing at the distal and proximal ends. The distal tip of the safety wire is made ultra-flexible in one direction by flattening a circular wire and immersing the wire into an electro-etching solution. Withdrawing the safety wire from the etch at a predetermined rate produces a uniformly tapered distal tip for the safety wire. In this manner, the transition between the ultra-flexible flattened distal tip and the relatively rigid circular body is smooth and uniform, having a carefully controlled cross-sectional area. Therefore, the possibility of breaking or kinking is minimized. That is, locations of preferential bending are eliminated.

Practice of the present invention results in a smooth guidewire with an integral safety-core wire, which is relatively rigid in the major portion of its length, which has a flexible distal tip, and which is free of preferential bending zones.

It is accordingly a broad object of the present invention to provide a guidewire having an ultra-smooth exterior surface.

A further object of the present invention is to provide a wound wire guidewire having an outer surface which is free from sharp edges.

Still a further object of the present invention is to provide a guidewire which exposes a minimum of foreign body microscopic surface area to the blood stream of the patient.

Another object of the present invention is to provide a guidewire having a combined core and safety wire which optimizes strength and flexibility.

Yet another object of the present invention is to provide a guidewire having a flexible distal tip, a relatively rigid body portion, and which is free from zones of preferential bending.

Still another object of the present invention is to provide a guidewire having a combined core and safety wire which has a smoothly tapered distal tip.

Yet another object of the present invention is to provide a guidewire assembly protected against distal fragments being lost in a patient's body.

A further object of the present invention is to provide a method of fabricating a guidewire such as that forming a part of the present invention.

These and other objects of the present invention, as well as many of the attendant advantages thereof, will become more readily apparent when reference is made to the following description taken in conjunction with the accompanying drawings.

BRIEF DESCRIPTION OF THE DRAWINGS

FIGS. 1a and 1b show the general features of the inventive and conventional guidewires respectively;

FIGS. 2a through 2c represent sequential steps in the manufacture of a coiled flatwire guidewire according to the teachings of the present invention;

FIGS. 3a and 3b illustrate the steps in an alternative method of manufacturing a coiled flatwire guidewire according to the teachings of the present invention;

FIGS. 4a through 4d illustrate the steps in the manufacture of a safety wire in accordance with the teachings of the present invention; and FIGS. 5a through 5f represent a safety wire formed in accordance with the teachings of the present invention.

DETAILED DESCRIPTION OF THE DRAWINGS

An elongated guidewire 10, constructed in accordance with the teachings of the present invention, is shown in FIG. 1a. The guidewire 10 comprises an elongated body with a proximal portion 14 and a distal tip portion 16. A combined core and safety wire 18 extends from the proximal end 14 to the distal end 16 of the guidewire 10. The body of the guidewire 10 takes the form of a coil spring, and is developed from a wound wire, such as a flatwire. One coil is indicated at 20. The safety core wire 18 is welded, or in some other fashion, connected to the respective ends of the wound body of the guidewire 10, as shown at 80 and 21.

FIG. 1b shows the corresponding features of a commonly used guidewire where 77 is the core wire and 78 is the safety wire. Area 79 is subject to preferential flexion due to the ending of the core wire.

FIGS. 2a, 2b, and 2c illustrate the steps in an inventive process for manufacturing a guidewire having an ultra-smooth outer surface.

In FIG. 2a, there is illustrated a flatwire 22, having a rectangular cross section. As shown in FIG. 2a, the flatwire 22 has not yet been wound into the spiral which defines the casing of guidewire 10. The unwound flatwire 22 is first coated with a lubricating agent 23, such as Teflon, and then appears as illustrated in FIG. 2b. After the wire is coated with lubricant 23, a suitable winding, or coiling apparatus is employed to wind the coated wire into a spiral. Typical dimensions for lengths "a" and "b" of wire 22 are 0.012 by 0.006 inches, respectively. The longer dimension of the flatwire, when coiled, defines the outer surface of the guidewire 10. This is illustrated in FIG. 2c. In this figure it can be seen that the outer surfaces of the respective coils of the flatwire take a concave shape or at best present leading and trailing edges when flatwire is used. This is due to internal stresses arising from the coiling of the flatwire, and result in the formation of relatively sharp edges, 24 and 26. Coating 23 also assumes a concave shape and has edges 24' amd 26' on each coil, corresponding to the edges 24 and 26 of the flatwire. The coating 23 is applied in a liquid state that subsequently hardens. Said coating naturally assumes a more rounded edge than the underlying raw metal. Should coating 23 be of an open cell microporous plastic nature, such a coating would be softer and less traumatic to blood vessel's intima and in addition could be a reservoir for an anticoagulant fluid such as a heparin solution or suspension that could slowly leach from the guidewire surface providing thromboresistance. The angiographer could infuse the solution into the plastic simply by pulling the guidewire through a compression die located in an anticoagulant solution. Such a guidewire may have to be inserted into the body through an arteriotomy insertion sheath so as not to anticoagulate the arteriotomy site.

Were it not for the lubricating or anticoagulant reservoir coating 23, the edges 24 and 26 on each coil would present sharp corners tending to traumatize body tissue or blood vessels during insertion or removal of the guidewire. The coating 23 absorbs some of the effects of the edges 24 and 26, with the corresponding edges 24' and 26' of the coating beng relatively smooth.

With wire 22 coated prior to the coiling process, coiling the flatwire into the body of the guidewire may be accomplished as is customary. Then, the guidewire is sterilized prior to use. In this manner, even though the guidewire undergoes twisting and bending motions during insertion, guiding and extraction, the coating remains integral. With this inventive guidewire, relative motion between adjacent coils is permitted without stressing the coating on the respective coils. In the prior art guidewires which are coated after winding, movement between adjacent coils introduces severe stresses on the coating material with resultant breakage between respective windings.

The steps involved in an alternative method of forming a catheter guidewire having an ultra-smooth outer surface are illustrated in FIGS. 3a and 3b.

FIG. 3a illustrates both the first step of the alternative inventive procedure as well as one method that has been attempted to achieve macro-smoothness of a guidewire. In this method, an uncoated stainless steel flatwire is wound into a spring and subsequently mechanically ground. As can be seen, though the concave shape of the coils can be virtually eliminated, minute surface irregularities still remain. In FIG. 3a, a coiled flatwire is illustrated at 30, surface irregularities are shown at 32, and the inter-coil spaces designated at 34.

FIG. 3b illustrates a guidewire manufactured in accordance with the teachings of the present invention. First, a flatwire is coiled to form a spiral guidewire, and then is mechanically ground to take the configuration of FIG. 3a. Finally, the roughened surface of the spiral is subjected to an electropolishing operation to remove any remaining roughness as well as providing edge smoothing. For example, 3 to 5 volts in an 80 to 100% solution of phosphoric acid produces a polished, minimum surface area surface. Increasing the voltage to between 10 and 20 volts and reducing the concentration of phosphoric acid to 50–60% removes metal much faster but has less of a polishing effect. As can be seen, the electropolishing operation exaggerates the inter-coil spaces 34 of FIG.3a, shown at 36 in FIG. 3b, but results in a surface 38 which is virtually free from irregularities.

A safety-core wire suitable for use with guidewire 10 is shown in FIG. 4d and denoted by the numeral 50 (18 in FIG. 1).

Safety-core wire 50 comprises an essentially flat expanded distal tip portion 81, a uniform flexible portion 52, a circular body or shank portion 54, and a smoothly tapering transition region 56. The result is an extremely flexible distal, or leading tip 52 and 81, a transition region 56 gradually increasing in stiffness from the distal to the proximal regions and a stiff shank 54 suitable for use as a core wire to add stiffness to the associated guidewire casing. The safety-core wire is welded to the guidewire casing at both its proximal and distal ends.

With reference now to FIGS. 4a through 4d, the steps involved in manufacturing the inventive safety wire indicated at 18 in FIG. 1 and in greater detail at 50 in FIG. 4d, will be described. FIG. 4a illustrates an elongated wire 60 having, for example, a circular cross-section. One end of wire 60, the distal end, is flattened by the application of high pressures by means of forming dies. The flattened distal end is indicated at 70 in FIG. 4b, and is illustrated in cross-section in FIG. 4c. The application of pressures results in the development of relatively flat opposed surfaces 71 and transition ramps 72. The distal region of the flattened wire illustrated in FIG. 4b is then immersed into and then slowly withdrawn from an electro-etching/polishing solution. Alternatively, the wire may be partially immersed and then slowly immersed further into an electro-etching/polishing solution. the important factor is that for a given wire position the time spent in the solution is proportional to the amount of metal that should be removed. Typically, the safety-core is started with a short distal section (uniform flexible portion 52) in the solution and the cross-sectioned area transition zone is gradually immersed. If the safety core is withdrawn, the entire distal section to be formed is inserted in the solution and the transition zone is gradually withdrawn. The slow removal or immersion of the distal end of the wire 70 from or into the etching bath, on the other hand, results in a gradual tapering and cross-sectional area modification over the transition zone 56 to the distal flexible region 52.

FIGS. 5b through 5f represent sections of the distal region of the electropolished wire 50 as shown in FIG. 5a. FIG. 5b is a cross section of the wire 50 taken along the line b—b of FIG. 5a; FIG. 5c is a cross section taken along line c—c of FIG. 5a, and so forth. As can be seen the wire 50 gradually tapers from a substantially circular cross section as illustrated in FIG. 5b, to a smooth-surfaced generally elliptical section as illustrated in FIG. 5e. FIG. 5f shows the distal diameter that is enlarged over the cross section shown in adjacent FIG. 5e which is accomplished by shielding the distal wire portion during the electro-etch/polish process. This increased cross-sectional area compensates for wire strength loss during the welding process that connects the safety core to the casing spring at the guidewire tip. Without the enlarged safety core, tip welding heat annealing would produce a weak area in the 5e region.

In the manner described above, the most distal end of the core-safety wire 50 has a high degree of flexibility in one direction, allowing the associated guidewire to easily follow the tortuous path of the human vascular system. At the same time, the more proximal body region 54 of the safety-core wire 50 is less flexible, and capable of adding the necessary stiffness for propelling the guidewire through the vascular system. Most important is the fact that the relatively rigid body of the safety-core wire 50 is gradually transformed into a highly flexible distal region. Because of the gradual transition, regions of preferential bending and breaking are eliminated.

The safety-core wire illustrated in FIG. 4 and 5 may typically have a cross-sectional diameter of from 15 to 18 mils in the region of section b—b, diminishing to a minimum diameter of approximately 4 mils at section 5e. The ramp 72 of FIG. 4b is on the order of approximately 1° with respect to the center line of the wire, and extends over a distance of approximately ½ inch. It has been found that a distance of from 3 to 6 inches between section b—b and the guidewire tip is sufficient lengthof guidewire tip flexibility.

Above, there has been provided a description of the inventive smooth-surfaced guidewire having a combined core and safety wire associated therewith. The inventive guidewire has an ultra-smooth outer surface, resulting from the application of a lubricating coating prior to winding, or by first grinding and then electropolishing a wound metallic base. The inventive safety-core wire comprises a main body having a relatively uniform cross section, such as a circular cross section, and a smoothly and uniformly tapering distal tip which is formed from first flattening and then electropolishing techniques. It should be appreciated that these embodiments of the present invention have been described for purposes of illustration only, and are in no way intended to be limiting. Rather, it is the intention that the present invention be limited only as defined in the appended claims.

I claim:

1. A guidewire adapted to guide a catheter into the body of a patient, the guidewire comprising: an elongated outer casing defined by an elongated rectangular flatwire having a width dimension and a height dimension less than said width dimension and having been wound into a coil spring wherein the surface of said outer casing is defined by consecutive coils of contacting widths; and a coating of coating material completely encasing the the flatwire which defines the coils of the coil spring; wherein said flatwire is coated prior to being wound.

2. The guidewire of claim 1, wherein said coating material is a lubricant such as Teflon.

3. The guidewire of claim 1 wherein said coating is porous and capable of serving as a fluid reservoir.

4. A guidewire adapted to guide a catheter into the body of a patient, the guidewire comprising: an elongated rectangular flatwire having a width dimension and a height dimension less than said width dimension and having been wound into a coil spring; wherein the surface of said outer casing is defined by consecutive coils of contacting widths; wherein the surface of said coil spring is mechanically ground to remove gross irregularities therefrom; and wherein the surface of said coil spring is subsequently electropolished to remove microscopic irregularities therefrom.

5. A guidewire adapted to guide an angiographic catheter into the body of a patient, the guidewire comprising: an elongated, flexible outer casing; and a combined core and safety wire extending longitudinally within said outer casing and attached thereto at the respective ends thereof; said core and safety wire having a flexible main body and an ultra-flexible tip, wherein the ultra-flexible tip is defined by a region of smoothly tapering cross-sectional area extending from a location on said main body toward one end thereof and a generally linear region of uniform cross-sectional area between said region of tapering cross-sectional area and said one end, said region of generally uniform cross-sectional area having a generally ellipitcal cross section with a major dimension being larger than a transverse minor dimension.

6. The guidewire of claim 5, wherein said core and safety wire includes a region of enlarged cross-sectional area at said one end to facilitate attachment to said outer casing, having a cross-sectional area larger than that of said region of tapering cross-sectional area nearest said one end.

7. The guidewire of claim 5, wherein the cross-sectional area of the core and safety wire tapers from a given area in the region of said main body to on the order of one-seventh said given area at said one end thereof.

8. The guidewire of claim 5, wherein said region of smoothly tapering cross-sectional area is on the order of three to 6 inches long.

9. The guidewire of claim 5, wherein said region of uniform cross-sectional area is on the order of 1 to 2 inches long.

10. The guidewire of claim 5, wherein said core and safety wire is argon arc welded to said outer casing.

* * * * *